United States Patent [19]
Maas

[11] 4,041,328
[45] Aug. 9, 1977

[54] ARRANGEMENT FOR THE DETERMINATION AND VISUALIZATION OF MEASURING SIGNALS

[75] Inventor: Michael Maas, Uttenreuth, Germany

[73] Assignee: Siemens Aktiengesellschaft, Berlin & Munich, Germany

[21] Appl. No.: 631,395

[22] Filed: Nov. 12, 1975

[30] Foreign Application Priority Data

Nov. 19, 1974    Germany ............................ 2454839

[51] Int. Cl.² .......................... H03K 5/20; A61B 5/04
[52] U.S. Cl. .................................... 307/351; 307/358; 328/149; 328/167; 128/2.06 A
[58] Field of Search ............ 307/235 A, 235 C, 235 J, 307/263, 264, 293, 294, 228, 255, 235 N, 235 T, 235 W; 328/146, 148, 149, 167, 185, 127; 128/1 D, 419 PT, 2.06 A, 2.06 R

[56] References Cited
U.S. PATENT DOCUMENTS

| | | | |
|---|---|---|---|
| 3,491,200 | 1/1970 | Wisnieff | 328/185 |
| 3,767,939 | 10/1973 | Chamran et al. | 328/167 |
| 3,816,636 | 6/1974 | Peltz | 307/263 |

*Primary Examiner*—John Zazworsky
*Assistant Examiner*—Marcus S. Rasco
*Attorney, Agent, or Firm*—Hill, Gross, Simpson, Van Santen, Steadman, Chiara & Simpson

[57] ABSTRACT

An arrangement for the determination and visualization of measuring signals having incident or thrown-in narrow and high-amplitudinal voltage peaks, in particular EKG signals which have pacemaker impulses superimposed thereon, including an RC-filter connected into the measuring signal path, a recognition element for recognizing the signal peaks, and an apparatus for the visual recording of the signals.

5 Claims, 2 Drawing Figures

ARRANGEMENT FOR THE DETERMINATION AND VISUALIZATION OF MEASURING SIGNALS

FIELD OF THE INVENTION

The present invention relates to an arrangement for the determination and visualization of measuring signals having incident or thrown-in narrow and high-amplitudinal voltage peaks, in particular EKG signals which have pacemaker impulses superimposed thereon, including an RC-filter connected into the measuring signal path, a recognition element for recognizing the signal peaks, and an apparatus for the visual recording of the signals.

The signal measurement technology, frequently encountered are voltage peaks which are superimposed on an intelligence or information signal due to interferences. In the normal instance it is consequently attempted to suppress those types of peaks which occur within the usable or intelligence signal. However, in actual practice there are also instances in which the suppression, or respectively extensive attenuation, of such voltage or current peaks is not desired but, in contrast, determines these peaks, and together with the actual usable or information measuring signal, records these, for example, on a recorder, oscillograph or the like. Such a case occurs, for example, in electromedicine during the monitoring of heart patients whose heart actions are supported or controlled through stimulating impulses, for example, by means of a heart pacemaker (pacemaker impulses). It is hereby desired that the stimulating impulses be determined in conjunction with the electrocardiogram of the patient and then rendered visible. The watching physician may then be able to control the recording, for example, the success of the stimulative support.

The recording of extremely narrow and high-amplitudinal voltage peaks — for instance, pacemaker impulses evidence, at a base width of maximum 0.8 ms an amplitude which consists of about forty times a normal R-display, — will, however, cause not insignificant difficulties, since normal recorders, for attaining the required high recording speeds, are in general too slow and will also lead at rapid vertical deflection of the electron beam of inertialess oscillographs images which are weak in brightness from which the peaks can only again be recognized with extreme difficulty.

DISCUSSION OF THE PRIOR ART

In order to render visible at least the location and the occurrence timepoints of the peaks particularly in the EKG diagnosis, there has heretofore been employed such processing arrangement through which with the recognition of a pacemaker impulse by means of an electronic recognition element, there is generated a standard impulse whose width is much greater in contrast with the base width of a pacemaker impulse, and whose amplitude is much lower in contrast to that of such a pacemaker impulse. This standard or normal impulse is then represented on the visualizing apparatus as evidence of the occurrence of a pacemaker impulse in conjunction with the EKG.

The representation of a pacemaker impulse as a normal or standard impulse has, however, the disadvantage in resulting in the loss of important information which are to be obtained from the pacemaker impulse such as, for example, with regard to the polarity thereof, amplitude, or also rate of increase. However, from those types of information there can be drawn important conclusions over the operative condition of the pacemaker.

SUMMARY OF THE INVENTION

Accordingly, it is an object of the present invention to provide an arrangement of the above-mentioned type which ameliorates or obviates the disadvantages encountered in the prior art.

The foregoing object is inventively attained by bridging or shunting switch means controlled by the recognition element which, upon the recognition of a high voltage peak through intermediary of the recognition element, will connect high voltage peaks directly to an associated filter condenser through by-passing of an ohmic resistance in an RC-filter and subsequently, after exceeding the amplitude of the signal peak while removing the resistance by-pass, will again connect the charged condenser, signal wise due to slow discharge, with the ohmic resistance.

In the arrangement according to the invention, a voltage peak is formed at the output of the RC-filter which is extensively widened with respect to its original strength, while still retaining, however, the original information with regard to polarity, rate of increase, and amplitude. That type of widened peak, however, may now be easily represented in a viewing picture, as well as on relatively slow recorders and also on oscillographs.

BRIEF DESCRIPTION OF THE DRAWINGS

Further advantages and details of the invention may be now ascertained from the following description of exemplary embodiments thereof, taken in conjunction with the accompanying drawings; in which.

DETAILED DESCRIPTION

Figure 1:
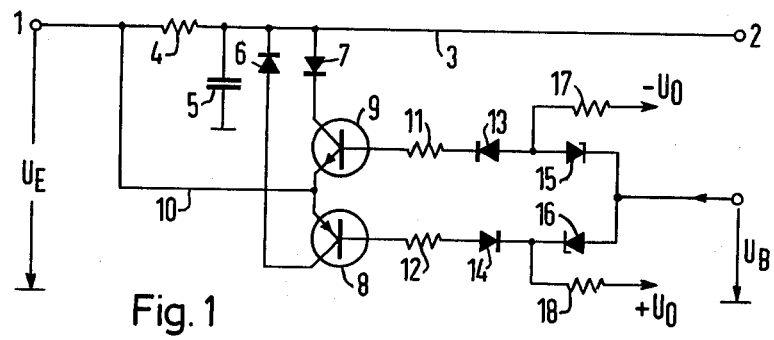
FIG. 1 is an exemplary embodiment of an arrangement constructed pursuant to the principle of the invention having a single RC-element.

Referring now in detail to the drawings, in FIG. 1 there is identified by reference numeral 1 the signal input of the circuit arrangement for a signal voltage $U_E$, for example, for an electrocardiogram, and reference numeral 2 identifies the associated signal output. Connected in the signal path or channel 3 between the input 1 and the output 2 is an RC-element having an ohmic resistance 4, and a parallel connected condenser 5. Furthermore located in the signal path 3 are the collectors of two transistors 8 and 9 through opposite poled diodes 6 and, respectively, 7. The emitters of these transistors 8 and 9 are connected through a common conduit 10 into the signal path 3 ahead of the input of the RC-element 4, 5. Thereby, the bases of the two resistors are connected to a reference voltage $U_B$ through limiting resistances 11, 12, as well as oppositely poled diodes 13 through 16 of which the diodes 15 and 16 are zener diodes, and others may be simple semiconductor diodes. Zener diodes 15 and 16 are presently connected with the voltages $-U_O$, respectively, $+U_O$ across resistances 17 and 18.

In the above-described circuit, the RC-element 4, 5 (low-pass) is so dimensioned that the signal cycle $U_E$, for example, the passage of the EKG signals from the signal input 1 to the signal output 2 is not substantially falsified. Furthermore, the reference voltage $U_B$ is so selected that also relatively high use or information signal amplitudes of the signal $U_E$, for instance relatively high R-displays in the case of an electrocardiogram, will be without any influence on the switching relationship of the transistors 8 and 9. However, if extraordinarily high-amplitudinal voltage peaks occur in the use signal $U_E$, which exceed the difference between the input voltage $U_E$ and the reference voltage $U_B$ by a predetermined voltage amount $U_S$, which is determined through the zener voltage of the zener diodes 15 and respectively 16, the gate voltage of the diodes 13 and respectively 14, the voltage drop-off at the limiting resistances 11 and respectively 12, and the emitter-base voltage of the transistors 8 and respectively 9, which is present in the case of EKG signals, for example, with the occurrence of pacemaker impulses, then at a positive voltage peak the transistor 8, and contrastingly at a negative voltage peak the transistor 9, is controlled into a conductive condition. This has the effect that the voltage peaks through by-passing of the resistance 4 (short-circuiting of the resistance 4) in the RC-element 4, 5, is directly conveyed to the condenser 5 of the RC-element through the conduit 10, the collector-emitter section of the currently conductive transistor 8 or 9, as well as through the correspondingly conductive diode 6 or 7. Since the ohmic resistance in the inlet circuit is extremely low, the condenser is thereby charged extremely rapidly to the peak voltage of the voltage peak. As soon as the voltage peak has exceeded its highest point, the presently conductive transistor 8 or 9 closes, and the condenser 5 is now slowly discharged across the ohmic resistance 4 to the potential of the use or information signal $U_E$. Appearing thus at the signal output 2 of the circuit arrangement according to FIG. 1, together with the use signal $U_E$, is voltage peak which, in comparison with the original, namely is extensively widened, while however evincing the same increase or rise period and, essentially, also the same amplitude as the original voltage peak. The width of the voltage peak which appears at the signal output 2 depends thereby merely upon the discharge-time constants of the RC element 4, 5. The peak impulse which is extensively broadened in this manner may now be comfortably rendered visible together with the original signal $U_E$ by means of recorders or oscillographs.

For example, selected as the reference potential $U_B$ there may be the ground potential. However, there is then present the danger that strong zero fluctuations of the original or basic signal $U_E$ may presently lead to an actuation of one of the transistors 8 or, respectively, 9. It is thereby more advantageous that the reference potential $U_E$ be corresponding correlated to eventually occurring direct-voltage fluctuations in the original or initial signal $U_E$.

Figure 2:
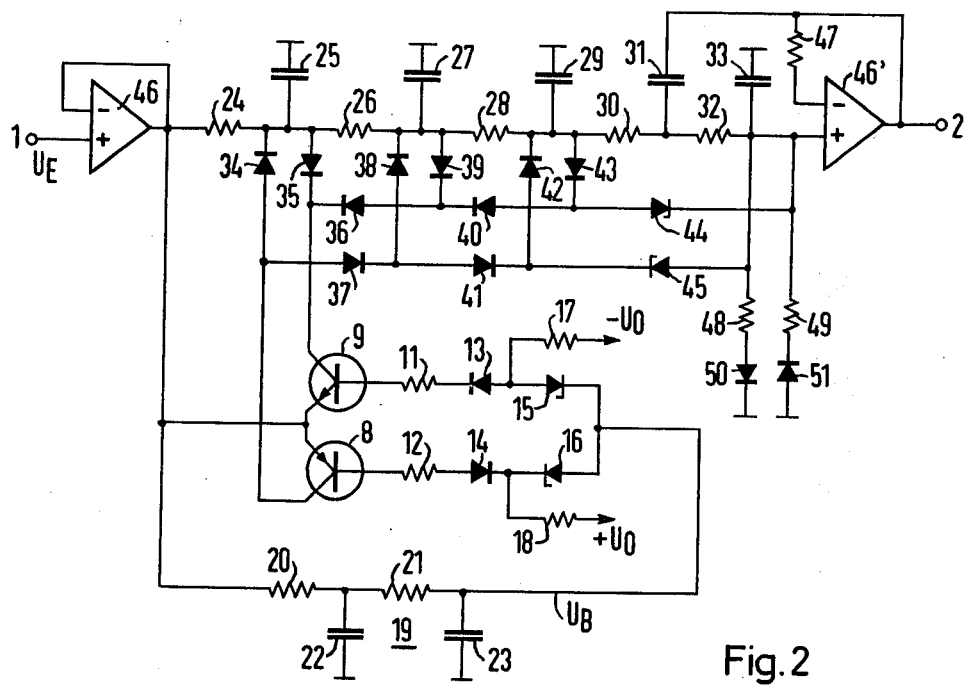
FIG. 2 is a modified embodiment similar to FIG. 1 containing a plurality of RC-elements.

The foregoing, for example, is carried in accordance with the circuit arrangement as shown in FIG. 2 through the intermediary of a low-pass filter 19 with the ohmic resistances 20 and 21, as well as capacitances 22 and 23 which are connected to the impulse voltage $U_E$, and which presently form a timewise median value from this impulse voltage $U_E$, which essentially represents the direct-voltage component. This median value of the use signal $U_E$ corresponds then to the utilized reference voltage value $U_B$. The threshold or limiting frequency of the low-pass filter 19 should be hereby selected at such a value which is essentially lower than that frequency which in time or period duration corresponds to the impulse width of the voltage peak.

The circuit arrangement according to FIG. 2 also distinguishes from the exemplary embodiment of FIG. 1 in that, in lieu of only a single RC-element, there is provided a total of five RC-elements 24 through 33 connected in series which in turn, are uncoupled from each other by diodes 34 through 45. Moreover, the diodes build an additional threshold between the individual stages. Through the utilization of a plurality of in that manner connected RC-elements, there is enlarged in particular the roof or cover width of the peak impulses which are to be reproduced.

The differential amplifier 46 represents an input amplifier for the signal voltage $U_E$. In contrast therewith, the differential amplifier 46' with the circuit elements 47 through 51 serves as an output amplifier for the current signal. Connected to the output of this amplifier 46', as also in the embodiment according to FIG. 1, is again a recording apparatus, for example, a recorder or oscillograph, for the reproduction of the current signals.

While there has been shown what is considered to be the preferred embodiment of the invention, it will be obvious that modifications may be made which come within the scope of the disclosure of the specification.

What is claimed is:

1. In an arrangement for the determination and visualization of measuring signals having incident narrow and high-amplitudinal voltage peaks, particularly EKG signals with superimposed pacemaker impulses, including an RC-filter connected into a measuring signal path and comprising at least one ohmic resistance and at least one filter condenser; two transistors having respective conductive paths connected across the ohmic resistance, the conductive path of one of said transistors providing a path for current flow of positive polarity between an input side of the RC-filter and the filter condenser bypassing said ohmic resistance in said RC-filter in a short-circuiting mode upon the occurrence of positive voltage peaks and the conductive path of the other transistor providing a path for current flow of negative polarity between the input side of the RC-filter and the filter condenser for bypassing said ohmic resistance in said RC-filter in a short-circuiting mode upon the occurrence of negative voltage peaks, each transistor in a conductive condition thereby directly connecting said measuring signal in said measuring signal path to said filter condenser, said transistors each having control inputs, and means providing a reference voltage connected to the control inputs of the transistors for controlling the conductive condition of said transistors responsive to the measuring signal voltage reaching respective positive and negative voltage peaks deviating from the reference voltage by a predetermined differential value.

2. An arrangement as claimed in claim 1, wherein said RC-filter comprises a plurality of RC-elements each having a series ohmic resistance and a shunt filter condenser, said RC-elements being connected in series, and diodes connecting each transistor with each of the filter condensers for decoupling said RC-elements with respect to each other and said transistors.

3. An arrangement as claimed in claim 1, with the paths for current flow of positive polarity and of negative polarity further including respective oppositely poled diodes interposed between the respective conductive paths of the respective transistors and the filter condenser.

4. An arrangement as claimed in claim 1, with said reference voltage providing means comprising a common terminal for receiving the reference voltage, and comprising respective series circuits connected between the common terminal and the control inputs of the respective transistors, each series circuit including a Zener diode, a semiconductor diode, and a limiting resistance means, the predetermined differential value being determined in part by the Zener voltage of said Zener diodes.

5. An arrangement as claimed in claim 1, wherein said reference voltage providing means is a low pass filter to provide a mean time value of the measuring signal voltage obtained through signal integration.

* * * * *